United States Patent
McPherson et al.

(10) Patent No.: US 8,231,616 B2
(45) Date of Patent: *Jul. 31, 2012

(54) TRANSFORMER FOR RF VOLTAGE SENSING

(75) Inventors: James W. McPherson, Boulder, CO (US); Lewis Puterbaugh, Longmont, CO (US)

(73) Assignee: Covidien AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/861,618

(22) Filed: Aug. 23, 2010

(65) Prior Publication Data

US 2010/0318079 A1  Dec. 16, 2010

Related U.S. Application Data

(63) Continuation of application No. 11/529,416, filed on Sep. 28, 2006, now Pat. No. 7,794,457.

(51) Int. Cl.
*A61B 18/04* (2006.01)
*A61B 18/12* (2006.01)
*A61B 18/14* (2006.01)
*H01F 27/28* (2006.01)
*H01F 27/29* (2006.01)

(52) U.S. Cl. .......... 606/34; 336/182; 336/220; 336/222

(58) Field of Classification Search .................. 336/182, 336/220, 222; 606/34
See application file for complete search history.

(56) References Cited

U.S. PATENT DOCUMENTS

| | | |
|---|---|---|
| 1,787,709 A | 1/1931 | Wappler |
| 1,813,902 A | 7/1931 | Bovie |
| 1,841,968 A | 1/1932 | Lowry |
| 1,863,118 A | 6/1932 | Liebel |
| 1,945,867 A | 2/1934 | Rawls |
| 2,827,056 A | 3/1958 | Degelman |
| 2,849,611 A | 8/1958 | Adams |
| 3,058,470 A | 10/1962 | Seeliger et al. |
| 3,089,496 A | 5/1963 | Degelman |
| 3,154,365 A | 10/1964 | Crimmins |
| 3,163,165 A | 12/1964 | Islikawa |
| 3,252,052 A | 5/1966 | Nash |
| 3,391,351 A | 7/1968 | Trent |
| 3,413,480 A | 11/1968 | Biard et al. |
| 3,436,563 A | 4/1969 | Regitz |
| 3,439,253 A | 4/1969 | Piteo |
| 3,439,680 A | 4/1969 | Thomas, Jr. |
| 3,461,874 A | 8/1969 | Martinez |
| 3,471,770 A | 10/1969 | Haire |

(Continued)

FOREIGN PATENT DOCUMENTS

DE   179607   3/1905

(Continued)

OTHER PUBLICATIONS

U.S. Appl. No. 6,878,148, filed Apr. 12, 2005, Goble et al. (withdrawn).

(Continued)

*Primary Examiner* — Roy Gibson
*Assistant Examiner* — Kaitlyn Smith

(57) ABSTRACT

An electrosurgical system is disclosed. The electrosurgical system includes a multiple-secondary transformer configured for sensing voltage. The multiple-secondary transformer includes a primary winding coupled to an active terminal and a return terminal of the electrosurgical system and a plurality of secondary windings. Each of the secondary windings is configured to transform the radio frequency voltage into a sensed voltage. Each of the secondary windings includes an output coupled to a sensor circuit and configured to transmit the sensed voltage to the sensor circuit.

20 Claims, 2 Drawing Sheets

U.S. PATENT DOCUMENTS

| | | |
|---|---|---|
| 3,478,744 A | 11/1969 | Leiter |
| 3,486,115 A | 12/1969 | Anderson |
| 3,495,584 A | 2/1970 | Schwalm |
| 3,513,353 A | 5/1970 | Lansch |
| 3,514,689 A | 5/1970 | Giannamore |
| 3,515,943 A | 6/1970 | Warrington |
| 3,551,786 A | 12/1970 | Van Gulik |
| 3,562,623 A | 2/1971 | Farnsworth |
| 3,571,644 A | 3/1971 | Jakoubovitch |
| 3,589,363 A | 6/1971 | Banko |
| 3,595,221 A | 7/1971 | Blackett |
| 3,601,126 A | 8/1971 | Estes |
| 3,611,053 A | 10/1971 | Rowell |
| 3,641,422 A | 2/1972 | Farnsworth et al. |
| 3,642,008 A | 2/1972 | Bolduc |
| 3,662,151 A | 5/1972 | Haffey |
| 3,675,655 A | 7/1972 | Sittner |
| 3,683,923 A | 8/1972 | Anderson |
| 3,693,613 A | 9/1972 | Kelman |
| 3,697,808 A | 10/1972 | Lee |
| 3,699,967 A | 10/1972 | Anderson |
| 3,720,896 A | 3/1973 | Bierlein |
| 3,743,918 A | 7/1973 | Maitre |
| 3,766,434 A | 10/1973 | Sherman |
| 3,768,019 A | 10/1973 | Podowski |
| 3,768,482 A | 10/1973 | Shaw |
| 3,801,766 A | 4/1974 | Morrison, Jr. |
| 3,801,800 A | 4/1974 | Newton |
| 3,812,858 A | 5/1974 | Oringer |
| 3,815,015 A | 6/1974 | Swin et al. |
| 3,826,263 A | 7/1974 | Cage et al. |
| 3,848,600 A | 11/1974 | Patrick, Jr. et al. |
| 3,870,047 A | 3/1975 | Gonser |
| 3,875,945 A | 4/1975 | Friedman |
| 3,885,569 A | 5/1975 | Judson |
| 3,897,787 A | 8/1975 | Ikuno et al. |
| 3,897,788 A | 8/1975 | Newton |
| 3,898,554 A | 8/1975 | Knudsen |
| 3,905,373 A | 9/1975 | Gonser |
| 3,908,176 A | 9/1975 | De Boer et al. |
| 3,913,583 A | 10/1975 | Bross |
| 3,923,063 A | 12/1975 | Andrews et al. |
| 3,933,157 A | 1/1976 | Bjurwill et al. |
| 3,946,738 A | 3/1976 | Newton et al. |
| 3,952,748 A | 4/1976 | Kaliher et al. |
| 3,963,030 A | 6/1976 | Newton |
| 3,964,487 A | 6/1976 | Judson |
| 3,971,365 A | 7/1976 | Smith |
| 3,978,393 A | 8/1976 | Wisner et al. |
| 3,980,085 A | 9/1976 | Ikuno |
| 3,998,538 A | 12/1976 | Urso et al. |
| 4,005,714 A | 2/1977 | Hilebrandt |
| 4,024,467 A | 5/1977 | Andrews et al. |
| 4,041,952 A | 8/1977 | Morrison, Jr. et al. |
| 4,051,855 A | 10/1977 | Schneiderman |
| 4,074,719 A | 2/1978 | Semm |
| 4,092,986 A | 6/1978 | Schneiderman |
| 4,094,320 A | 6/1978 | Newton et al. |
| 4,097,773 A | 6/1978 | Lindmark |
| 4,102,341 A | 7/1978 | Ikuno et al. |
| 4,114,623 A | 9/1978 | Meinke et al. |
| 4,121,590 A | 10/1978 | Gonser |
| 4,123,673 A | 10/1978 | Gonser |
| 4,126,137 A | 11/1978 | Archibald |
| 4,171,700 A | 10/1979 | Farin |
| 4,188,927 A | 2/1980 | Harris |
| 4,191,188 A | 3/1980 | Belt et al. |
| 4,196,734 A | 4/1980 | Harris |
| 4,200,104 A | 4/1980 | Harris |
| 4,200,105 A | 4/1980 | Gosner |
| 4,204,549 A | 5/1980 | Paglione |
| 4,209,018 A | 6/1980 | Meinke et al. |
| 4,228,809 A | 10/1980 | Paglione |
| 4,229,714 A | 10/1980 | Yu |
| 4,231,372 A | 11/1980 | Newton |
| 4,232,676 A | 11/1980 | Herczog |
| 4,237,887 A | 12/1980 | Gosner |
| 4,247,815 A | 1/1981 | Larsen et al. |
| 4,281,373 A | 7/1981 | Mabille |
| 4,287,557 A | 9/1981 | Brehse |
| 4,296,413 A | 10/1981 | Milkovic |
| 4,303,073 A | 12/1981 | Archibald |
| 4,311,154 A | 1/1982 | Sterzer et al. |
| 4,314,559 A | 2/1982 | Allen |
| 4,321,926 A | 3/1982 | Roge |
| 4,334,539 A | 6/1982 | Childs et al. |
| 4,343,308 A | 8/1982 | Gross |
| 4,359,626 A | 11/1982 | Potter |
| 4,372,315 A | 2/1983 | Shapiro et al. |
| 4,376,263 A | 3/1983 | Pittroff et al. |
| 4,378,801 A | 4/1983 | Oosten |
| 4,384,582 A | 5/1983 | Watt |
| 4,397,314 A | 8/1983 | Vaguine |
| 4,411,266 A | 10/1983 | Cosman |
| 4,416,276 A | 11/1983 | Newton et al. |
| 4,416,277 A | 11/1983 | Newton et al. |
| 4,429,694 A | 2/1984 | McGreevy |
| 4,436,091 A | 3/1984 | Banko |
| 4,437,464 A | 3/1984 | Crow |
| 4,438,766 A | 3/1984 | Bowers |
| 4,463,759 A | 8/1984 | Garito et al. |
| 4,472,661 A | 9/1984 | Culver |
| 4,474,179 A | 10/1984 | Koch |
| 4,492,231 A | 1/1985 | Auth |
| 4,492,832 A | 1/1985 | Taylor |
| 4,494,541 A | 1/1985 | Archibald |
| 4,514,619 A | 4/1985 | Kugelman |
| 4,520,818 A | 6/1985 | Mickiewicz |
| 4,532,924 A | 8/1985 | Auth et al. |
| 4,559,496 A | 12/1985 | Harnden, Jr. et al. |
| 4,559,943 A | 12/1985 | Bowers |
| 4,565,200 A | 1/1986 | Cosman |
| 4,566,454 A | 1/1986 | Mehl et al. |
| 4,569,345 A | 2/1986 | Manes |
| 4,572,190 A | 2/1986 | Azam et al. |
| 4,582,057 A | 4/1986 | Auth et al. |
| 4,586,120 A | 4/1986 | Malik et al. |
| 4,590,934 A | 5/1986 | Malis et al. |
| 4,595,248 A | 6/1986 | Brown |
| 4,608,977 A | 9/1986 | Brown |
| 4,615,330 A | 10/1986 | Nagasaki et al. |
| 4,630,218 A | 12/1986 | Hurley |
| 4,632,109 A | 12/1986 | Patterson |
| 4,644,955 A | 2/1987 | Mioduski |
| 4,651,264 A | 3/1987 | Shiao-Chung Hu |
| 4,651,280 A | 3/1987 | Chang et al. |
| 4,657,015 A | 4/1987 | Irnich |
| 4,658,815 A | 4/1987 | Farin et al. |
| 4,658,819 A | 4/1987 | Harris et al. |
| 4,658,820 A | 4/1987 | Klicek |
| 4,662,383 A | 5/1987 | Sogawa et al. |
| 4,691,703 A | 9/1987 | Auth et al. |
| 4,727,874 A | 3/1988 | Bowers et al. |
| 4,735,204 A | 4/1988 | Sussman et al. |
| 4,739,759 A | 4/1988 | Rexroth et al. |
| 4,741,334 A | 5/1988 | Irnich |
| 4,741,348 A | 5/1988 | Kikuchi et al. |
| 4,744,372 A | 5/1988 | Kikuchi et al. |
| 4,754,757 A | 7/1988 | Feucht |
| 4,767,999 A | 8/1988 | VerPlanck |
| 4,768,969 A | 9/1988 | Bauer et al. |
| 4,785,829 A | 11/1988 | Convert et al. |
| 4,788,634 A | 11/1988 | Schlecht et al. |
| 4,805,621 A | 2/1989 | Heinze et al. |
| 4,818,954 A | 4/1989 | Flachenecker et al. |
| 4,827,927 A | 5/1989 | Newton |
| 4,848,335 A | 7/1989 | Manes |
| 4,860,745 A | 8/1989 | Farin et al. |
| 4,862,889 A | 9/1989 | Feucht |
| 4,887,199 A | 12/1989 | Whittle |
| 4,890,610 A | 1/1990 | Kirwan et al. |
| 4,903,696 A | 2/1990 | Stasz et al. |
| 4,907,589 A | 3/1990 | Cosman |
| 4,922,210 A | 5/1990 | Flachenecker et al. |
| 4,925,089 A | 5/1990 | Chaparro et al. |
| 4,931,047 A | 6/1990 | Broadwin et al. |
| 4,931,717 A | 6/1990 | Gray et al. |

| Patent | Date | Name |
|---|---|---|
| 4,938,761 A | 7/1990 | Ensslin |
| 4,942,313 A | 7/1990 | Kinzel |
| 4,959,606 A | 9/1990 | Forge |
| 4,961,047 A | 10/1990 | Carder |
| 4,961,435 A | 10/1990 | Kitagawa et al. |
| 4,966,597 A | 10/1990 | Cosman |
| 4,969,885 A | 11/1990 | Farin |
| 4,992,719 A | 2/1991 | Harvey |
| 4,993,430 A | 2/1991 | Shimoyama et al. |
| 4,995,877 A | 2/1991 | Ams et al. |
| 5,015,227 A | 5/1991 | Broadwin et al. |
| 5,024,668 A | 6/1991 | Peters et al. |
| 5,044,977 A | 9/1991 | Vindigni |
| 5,067,953 A | 11/1991 | Feucht |
| 5,075,839 A | 12/1991 | Fisher et al. |
| 5,087,257 A | 2/1992 | Farin |
| 5,099,840 A | 3/1992 | Goble et al. |
| 5,103,804 A | 4/1992 | Abele et al. |
| 5,108,389 A | 4/1992 | Cosmescu |
| 5,108,391 A | 4/1992 | Flachenecker |
| 5,119,284 A | 6/1992 | Fisher et al. |
| 5,122,137 A | 6/1992 | Lennox |
| 5,133,711 A | 7/1992 | Hagen |
| 5,151,102 A | 9/1992 | Kamiyama et al. |
| 5,152,762 A | 10/1992 | McElhenney |
| 5,157,603 A | 10/1992 | Scheller et al. |
| 5,160,334 A | 11/1992 | Billings et al. |
| 5,161,893 A | 11/1992 | Shigezawa et al. |
| 5,167,658 A | 12/1992 | Ensslin |
| 5,167,659 A | 12/1992 | Ohtomo et al. |
| 5,190,517 A | 3/1993 | Zieve et al. |
| 5,196,008 A | 3/1993 | Kuenecke |
| 5,196,009 A | 3/1993 | Kirwan, Jr. |
| 5,201,900 A | 4/1993 | Nardella |
| 5,207,691 A | 5/1993 | Nardella |
| 5,230,623 A | 7/1993 | Guthrie et al. |
| 5,233,515 A | 8/1993 | Cosman |
| 5,234,427 A | 8/1993 | Ohtomo et al. |
| 5,249,121 A | 9/1993 | Baum et al. |
| 5,249,585 A | 10/1993 | Turner et al. |
| 5,254,117 A | 10/1993 | Rigby et al. |
| RE34,432 E | 11/1993 | Bertrand |
| 5,267,994 A | 12/1993 | Gentelia et al. |
| 5,267,997 A | 12/1993 | Farin |
| 5,281,213 A | 1/1994 | Milder et al. |
| 5,282,840 A | 2/1994 | Hudrlik |
| 5,290,283 A | 3/1994 | Suda |
| 5,295,857 A | 3/1994 | Toly |
| 5,300,068 A | 4/1994 | Rosar et al. |
| 5,300,070 A | 4/1994 | Gentelia |
| 5,304,917 A | 4/1994 | Somerville |
| 5,318,563 A | 6/1994 | Malis et al. |
| 5,323,778 A | 6/1994 | Kandarpa et al. |
| 5,324,283 A | 6/1994 | Heckele |
| 5,330,518 A | 7/1994 | Neilson et al. |
| 5,334,183 A | 8/1994 | Wuchinich |
| 5,334,193 A | 8/1994 | Nardella |
| 5,341,807 A | 8/1994 | Nardella |
| 5,342,356 A | 8/1994 | Ellman |
| 5,342,357 A | 8/1994 | Nardella |
| 5,342,409 A | 8/1994 | Mullett |
| 5,346,406 A | 9/1994 | Hoffman et al. |
| 5,346,491 A | 9/1994 | Oertli |
| 5,348,554 A | 9/1994 | Imran et al. |
| 5,354,325 A | 10/1994 | Chive et al. |
| 5,364,392 A | 11/1994 | Warner et al. |
| 5,369,567 A | 11/1994 | Furuta et al. |
| 5,370,645 A | 12/1994 | Klicek et al. |
| 5,370,672 A | 12/1994 | Fowler et al. |
| 5,370,675 A | 12/1994 | Edwards et al. |
| 5,372,596 A | 12/1994 | Klicek et al. |
| 5,383,874 A | 1/1995 | Jackson |
| 5,383,876 A | 1/1995 | Nardella |
| 5,383,917 A | 1/1995 | Desai et al. |
| 5,385,148 A | 1/1995 | Lesh et al. |
| 5,400,267 A | 3/1995 | Denen et al. |
| 5,403,311 A | 4/1995 | Abele et al. |
| 5,403,312 A | 4/1995 | Yates et al. |
| 5,409,000 A | 4/1995 | Imran |
| 5,409,485 A | 4/1995 | Suda |
| 5,413,573 A | 5/1995 | Koivukangas |
| 5,414,238 A | 5/1995 | Steigerwald et al. |
| 5,417,719 A | 5/1995 | Hull et al. |
| 5,422,567 A | 6/1995 | Matsunaga |
| 5,422,926 A | 6/1995 | Smith et al. |
| 5,423,808 A | 6/1995 | Edwards et al. |
| 5,423,809 A | 6/1995 | Klicek |
| 5,423,810 A | 6/1995 | Goble et al. |
| 5,423,811 A | 6/1995 | Imran et al. |
| 5,425,704 A | 6/1995 | Sakurai et al. |
| 5,429,596 A | 7/1995 | Arias et al. |
| 5,430,434 A | 7/1995 | Lederer et al. |
| 5,432,459 A | 7/1995 | Thompson |
| 5,433,739 A | 7/1995 | Sluijter et al. |
| 5,436,566 A | 7/1995 | Thompson |
| 5,438,302 A | 8/1995 | Goble |
| 5,443,462 A | 8/1995 | Hannant |
| 5,443,463 A | 8/1995 | Stern et al. |
| 5,445,635 A | 8/1995 | Denen |
| 5,451,224 A | 9/1995 | Goble et al. |
| 5,452,725 A | 9/1995 | Martenson |
| 5,454,809 A | 10/1995 | Janssen |
| 5,458,597 A | 10/1995 | Edwards et al. |
| 5,462,521 A | 10/1995 | Brucker et al. |
| 5,472,441 A | 12/1995 | Edwards et al. |
| 5,472,443 A | 12/1995 | Cordis et al. |
| 5,474,464 A | 12/1995 | Drewnicki |
| 5,480,399 A | 1/1996 | Hebborn |
| 5,483,952 A | 1/1996 | Aranyi |
| 5,496,312 A | 3/1996 | Klicek |
| 5,496,313 A | 3/1996 | Gentelia et al. |
| 5,496,314 A | 3/1996 | Eggers |
| 5,500,012 A | 3/1996 | Brucker et al. |
| 5,500,616 A | 3/1996 | Ochi |
| 5,511,993 A | 4/1996 | Yamada et al. |
| 5,514,129 A | 5/1996 | Smith |
| 5,520,684 A | 5/1996 | Imran |
| 5,531,774 A | 7/1996 | Schulman et al. |
| 5,534,018 A | 7/1996 | Wahlstrand et al. |
| 5,536,267 A | 7/1996 | Edwards et al. |
| 5,540,677 A | 7/1996 | Sinofsky |
| 5,540,681 A | 7/1996 | Strul et al. |
| 5,540,682 A | 7/1996 | Gardner et al. |
| 5,540,683 A | 7/1996 | Ichikawa |
| 5,540,684 A | 7/1996 | Hassler, Jr. |
| 5,541,376 A | 7/1996 | Ladtkow et al. |
| 5,545,161 A | 8/1996 | Imran |
| 5,556,396 A | 9/1996 | Cohen et al. |
| 5,558,671 A | 9/1996 | Yates |
| 5,562,720 A | 10/1996 | Stern et al. |
| 5,569,242 A | 10/1996 | Lax et al. |
| 5,571,147 A | 11/1996 | Sluijter et al. |
| 5,573,533 A | 11/1996 | Strul |
| 5,584,830 A | 12/1996 | Ladd et al. |
| 5,588,432 A | 12/1996 | Crowley |
| 5,596,466 A | 1/1997 | Ochi |
| 5,599,344 A | 2/1997 | Paterson |
| 5,599,345 A | 2/1997 | Edwards et al. |
| 5,599,348 A | 2/1997 | Gentelia et al. |
| 5,605,150 A | 2/1997 | Radons et al. |
| 5,609,560 A | 3/1997 | Ichikawa et al. |
| 5,613,966 A | 3/1997 | Makower et al. |
| 5,620,481 A | 4/1997 | Desai et al. |
| 5,626,575 A | 5/1997 | Crenner |
| 5,628,745 A | 5/1997 | Bek |
| 5,628,771 A | 5/1997 | Mizukawa et al. |
| 5,643,330 A | 7/1997 | Holsheimer et al. |
| 5,647,869 A | 7/1997 | Goble et al. |
| 5,647,871 A | 7/1997 | Levine et al. |
| 5,651,780 A | 7/1997 | Jackson et al. |
| 5,658,322 A | 8/1997 | Fleming |
| 5,660,567 A | 8/1997 | Nierlich et al. |
| 5,664,953 A | 9/1997 | Reylek |
| 5,674,217 A | 10/1997 | Wahlstrom et al. |
| 5,678,568 A | 10/1997 | Uchikubo et al. |
| 5,681,307 A | 10/1997 | McMahan |
| 5,685,840 A | 11/1997 | Schechter et al. |
| 5,688,267 A | 11/1997 | Panescu et al. |

| | | | | | | |
|---|---|---|---|---|---|---|
| 5,693,042 A | 12/1997 | Bioarski et al. | | 5,971,981 A | 10/1999 | Hill et al. |
| 5,693,078 A | 12/1997 | Desai et al. | | 5,976,128 A | 11/1999 | Schilling et al. |
| 5,694,304 A | 12/1997 | Telefus et al. | | 5,983,141 A | 11/1999 | Sluijter et al. |
| 5,695,494 A | 12/1997 | Becker | | 6,007,532 A | 12/1999 | Netherly |
| 5,696,441 A | 12/1997 | Mak et al. | | 6,010,499 A | 1/2000 | Cobb |
| 5,697,925 A | 12/1997 | Taylor | | 6,013,074 A | 1/2000 | Taylor |
| 5,697,927 A | 12/1997 | Imran et al. | | 6,014,581 A | 1/2000 | Whayne et al. |
| 5,702,386 A | 12/1997 | Stern et al. | | 6,017,338 A | 1/2000 | Brucker et al. |
| 5,702,429 A | 12/1997 | King | | 6,017,354 A | 1/2000 | Culp et al. |
| 5,707,369 A | 1/1998 | Vaitekunas et al. | | 6,022,346 A | 2/2000 | Panescu et al. |
| 5,712,772 A | 1/1998 | Telefus et al. | | 6,022,347 A | 2/2000 | Lindenmeier et al. |
| 5,713,896 A | 2/1998 | Nardella | | 6,033,399 A | 3/2000 | Gines |
| 5,718,246 A | 2/1998 | Vona | | 6,039,731 A | 3/2000 | Taylor et al. |
| 5,720,742 A | 2/1998 | Zacharias | | 6,039,732 A | 3/2000 | Ichikawa et al. |
| 5,720,744 A | 2/1998 | Eggleston et al. | | 6,041,260 A | 3/2000 | Stern et al. |
| 5,722,975 A | 3/1998 | Edwards et al. | | 6,044,283 A | 3/2000 | Fein et al. |
| 5,729,448 A | 3/1998 | Haynie et al. | | 6,053,910 A | 4/2000 | Fleenor |
| 5,733,281 A | 3/1998 | Nardella | | 6,053,912 A | 4/2000 | Panescu et al. |
| 5,735,846 A | 4/1998 | Panescu et al. | | 6,055,458 A | 4/2000 | Cochran et al. |
| 5,738,683 A | 4/1998 | Osypka | | 6,056,745 A | 5/2000 | Panescu et al. |
| 5,743,900 A | 4/1998 | Hara | | 6,056,746 A | 5/2000 | Goble et al. |
| 5,743,903 A | 4/1998 | Stern et al. | | 6,059,780 A | 5/2000 | Gough et al. |
| 5,749,869 A | 5/1998 | Lindenmeier et al. | | 6,059,781 A | 5/2000 | Yamanashi et al. |
| 5,749,871 A | 5/1998 | Hood et al. | | 6,063,075 A | 5/2000 | Mihori |
| 5,755,715 A | 5/1998 | Stern | | 6,063,078 A | 5/2000 | Wittkampf |
| 5,762,609 A | 6/1998 | Benaron et al. | | 6,066,137 A | 5/2000 | Greep |
| 5,766,153 A | 6/1998 | Eggers et al. | | 6,068,627 A | 5/2000 | Orszulak et al. |
| 5,766,165 A | 6/1998 | Gentelia et al. | | 6,074,089 A | 6/2000 | Hollander et al. |
| 5,769,847 A | 6/1998 | Panescu | | 6,074,386 A | 6/2000 | Goble et al. |
| 5,772,659 A | 6/1998 | Becker et al. | | 6,074,388 A | 6/2000 | Tockweiler et al. |
| 5,788,688 A | 8/1998 | Bauer et al. | | 6,080,149 A | 6/2000 | Huang et al. |
| 5,792,138 A | 8/1998 | Shipp | | 6,088,614 A | 7/2000 | Swanson |
| 5,797,902 A | 8/1998 | Netherly | | 6,090,123 A | 7/2000 | Culp et al. |
| 5,797,941 A | 8/1998 | Schulze et al. | | 6,093,186 A | 7/2000 | Goble |
| 5,807,253 A | 9/1998 | Dumoulin et al. | | 6,102,497 A | 8/2000 | Ehr et al. |
| 5,810,804 A | 9/1998 | Gough et al. | | 6,102,907 A | 8/2000 | Smethers et al. |
| 5,814,092 A | 9/1998 | King | | 6,106,524 A | 8/2000 | Eggers et al. |
| 5,817,091 A | 10/1998 | Nardella et al. | | 6,113,591 A | 9/2000 | Whayne et al. |
| 5,817,093 A | 10/1998 | Williamson, IV et al. | | 6,113,592 A | 9/2000 | Taylor |
| 5,820,568 A | 10/1998 | Willis | | 6,113,593 A | 9/2000 | Tu et al. |
| 5,827,271 A | 10/1998 | Bussey et al. | | 6,113,596 A | 9/2000 | Hooven |
| 5,830,212 A | 11/1998 | Cartmell | | 6,123,701 A | 9/2000 | Nezhat |
| 5,836,909 A | 11/1998 | Cosmescu | | 6,123,702 A | 9/2000 | Swanson et al. |
| 5,836,943 A | 11/1998 | Miller, III | | 6,132,429 A | 10/2000 | Baker |
| 5,836,990 A | 11/1998 | Li | | 6,142,992 A | 11/2000 | Cheng et al. |
| 5,843,019 A | 12/1998 | Eggers et al. | | 6,155,975 A | 12/2000 | Urich et al. |
| 5,843,075 A | 12/1998 | Taylor | | 6,162,184 A | 12/2000 | Swanson et al. |
| 5,846,236 A | 12/1998 | Lindenmeier et al. | | 6,162,217 A | 12/2000 | Kannenberg et al. |
| 5,849,010 A | 12/1998 | Wurzer et al. | | 6,165,169 A | 12/2000 | Panescu et al. |
| 5,853,409 A | 12/1998 | Swanson et al. | | 6,165,173 A | 12/2000 | Kamdar et al. |
| 5,860,832 A | 1/1999 | Wayt et al. | | 6,171,304 B1 | 1/2001 | Netherly et al. |
| 5,865,788 A | 2/1999 | Edwards et al. | | 6,183,468 B1 | 2/2001 | Swanson et al. |
| 5,868,737 A | 2/1999 | Taylor et al. | | 6,186,147 B1 | 2/2001 | Cobb |
| 5,868,739 A | 2/1999 | Lindenmeier et al. | | 6,188,211 B1 | 2/2001 | Rincon-Mora et al. |
| 5,868,740 A | 2/1999 | LeVeen et al. | | 6,193,713 B1 | 2/2001 | Geistert et al. |
| 5,871,481 A | 2/1999 | Kannenberg et al. | | 6,197,023 B1 | 3/2001 | Muntermann |
| 5,891,142 A | 4/1999 | Eggers et al. | | 6,203,541 B1 | 3/2001 | Keppel |
| 5,893,848 A | 4/1999 | Negus et al. | | 6,210,403 B1 | 4/2001 | Klicek |
| 5,897,552 A | 4/1999 | Edwards et al. | | 6,216,704 B1 | 4/2001 | Ingle et al. |
| 5,906,614 A | 5/1999 | Stern et al. | | 6,222,356 B1 | 4/2001 | Taghizadeh-Kaschani |
| 5,908,444 A | 6/1999 | Azure | | 6,228,078 B1 | 5/2001 | Eggers et al. |
| 5,913,882 A | 6/1999 | King | | 6,228,080 B1 | 5/2001 | Gines |
| 5,921,982 A | 7/1999 | Lesh et al. | | 6,228,081 B1 | 5/2001 | Goble |
| 5,925,070 A | 7/1999 | King et al. | | 6,231,569 B1 | 5/2001 | Bek |
| 5,931,836 A | 8/1999 | Hatta et al. | | 6,232,556 B1 | 5/2001 | Daugherty et al. |
| 5,935,124 A | 8/1999 | Klumb et al. | | 6,235,020 B1 | 5/2001 | Cheng et al. |
| 5,938,690 A | 8/1999 | Law et al. | | 6,235,022 B1 | 5/2001 | Hallock et al. |
| 5,944,553 A | 8/1999 | Yasui et al. | | 6,237,604 B1 | 5/2001 | Burnside et al. |
| 5,948,007 A | 9/1999 | Starkenbaum et al. | | 6,238,387 B1 | 5/2001 | Miller, III |
| 5,951,545 A | 9/1999 | Schilling | | 6,238,388 B1 | 5/2001 | Ellman |
| 5,951,546 A | 9/1999 | Lorentzen | | 6,241,723 B1 | 6/2001 | Heim et al. |
| 5,954,686 A | 9/1999 | Garito et al. | | 6,241,725 B1 | 6/2001 | Cosman |
| 5,954,717 A | 9/1999 | Behl et al. | | 6,243,654 B1 | 6/2001 | Johnson et al. |
| 5,954,719 A | 9/1999 | Chen et al. | | 6,245,061 B1 | 6/2001 | Panescu et al. |
| 5,957,961 A | 9/1999 | Maguire et al. | | 6,245,063 B1 | 6/2001 | Uphoff |
| 5,959,253 A | 9/1999 | Shinchi | | 6,245,065 B1 | 6/2001 | Panescu |
| 5,961,344 A | 10/1999 | Rosales et al. | | 6,246,912 B1 | 6/2001 | Sluijter et al. |
| 5,964,746 A | 10/1999 | McCary | | 6,251,106 B1 | 6/2001 | Becker et al. |
| 5,971,980 A | 10/1999 | Sherman | | 6,254,422 B1 | 7/2001 | Feye-Hohmann |

| | | |
|---|---|---|
| 6,258,085 B1 | 7/2001 | Eggleston |
| 6,261,285 B1 | 7/2001 | Novak |
| 6,261,286 B1 | 7/2001 | Goble et al. |
| 6,267,760 B1 | 7/2001 | Swanson |
| 6,273,886 B1 | 8/2001 | Edwards |
| 6,275,786 B1 | 8/2001 | Daners |
| 6,293,941 B1 | 9/2001 | Strul |
| 6,293,942 B1 | 9/2001 | Goble et al. |
| 6,293,943 B1 | 9/2001 | Panescu et al. |
| 6,296,636 B1 | 10/2001 | Cheng et al. |
| 6,306,131 B1 | 10/2001 | Hareyama et al. |
| 6,306,134 B1 | 10/2001 | Goble et al. |
| 6,309,386 B1 | 10/2001 | Bek |
| 6,322,558 B1 | 11/2001 | Taylor et al. |
| 6,325,799 B1 | 12/2001 | Goble |
| 6,329,778 B1 | 12/2001 | Culp et al. |
| 6,337,998 B1 | 1/2002 | Behl et al. |
| 6,338,657 B1 | 1/2002 | Harper et al. |
| 6,350,262 B1 | 2/2002 | Ashley |
| 6,358,245 B1 | 3/2002 | Edwards |
| 6,364,877 B1 | 4/2002 | Goble et al. |
| 6,370,408 B1 | 4/2002 | Merchant et al. |
| 6,371,963 B1 | 4/2002 | Nishtala et al. |
| 6,383,183 B1 | 5/2002 | Sekino et al. |
| 6,391,024 B1 | 5/2002 | Sun et al. |
| 6,398,779 B1 | 6/2002 | Buysse et al. |
| 6,398,781 B1 | 6/2002 | Goble et al. |
| 6,402,741 B1 | 6/2002 | Keppel et al. |
| 6,402,742 B1 | 6/2002 | Blewett et al. |
| 6,402,743 B1 | 6/2002 | Orszulak et al. |
| 6,402,748 B1 | 6/2002 | Schoenman et al. |
| 6,409,722 B1 | 6/2002 | Hoey et al. |
| 6,413,256 B1 | 7/2002 | Truckai et al. |
| 6,416,509 B1 | 7/2002 | Goble et al. |
| 6,422,896 B2 | 7/2002 | Aoki et al. |
| 6,423,057 B1 | 7/2002 | He et al. |
| 6,426,886 B1 | 7/2002 | Goder |
| 6,428,537 B1 | 8/2002 | Swanson et al. |
| 6,436,096 B1 | 8/2002 | Hareyama |
| 6,440,157 B1 | 8/2002 | Shigezawa et al. |
| 6,451,015 B1 | 9/2002 | Rittman, III et al. |
| 6,454,594 B2 | 9/2002 | Sawayanagi |
| 6,458,121 B1 | 10/2002 | Rosenstock et al. |
| 6,458,122 B1 | 10/2002 | Pozzato |
| 6,464,689 B1 | 10/2002 | Qin |
| 6,464,696 B1 | 10/2002 | Oyama |
| 6,468,270 B1 | 10/2002 | Hovda et al. |
| 6,468,273 B1 | 10/2002 | Leveen et al. |
| 6,482,201 B1 | 11/2002 | Olsen et al. |
| 6,488,678 B2 | 12/2002 | Sherman |
| 6,494,880 B1 | 12/2002 | Swanson et al. |
| 6,497,659 B1 | 12/2002 | Rafert |
| 6,498,466 B1 | 12/2002 | Edwards |
| 6,506,189 B1 | 1/2003 | Rittman, III et al. |
| 6,508,815 B1 | 1/2003 | Strul |
| 6,511,476 B2 | 1/2003 | Hareyama |
| 6,511,478 B1 | 1/2003 | Burnside |
| 6,517,538 B1 | 2/2003 | Jacob et al. |
| 6,522,931 B2 | 2/2003 | Manker et al. |
| 6,524,308 B1 | 2/2003 | Muller et al. |
| 6,537,272 B2 | 3/2003 | Christopherson et al. |
| 6,544,260 B1 | 4/2003 | Markel et al. |
| 6,546,270 B1 | 4/2003 | Goldin et al. |
| 6,547,786 B1 | 4/2003 | Goble |
| 6,557,559 B1 | 5/2003 | Eggers et al. |
| 6,558,376 B2 | 5/2003 | Bishop |
| 6,558,377 B2 | 5/2003 | Lee et al. |
| 6,560,470 B1 | 5/2003 | Pologe |
| 6,562,037 B2 | 5/2003 | Paton |
| 6,565,559 B2 | 5/2003 | Eggleston |
| 6,565,562 B1 | 5/2003 | Shah et al. |
| 6,575,969 B1 | 6/2003 | Rittman, III et al. |
| 6,578,579 B2 | 6/2003 | Burnside et al. |
| 6,579,288 B1 | 6/2003 | Swanson et al. |
| 6,582,427 B1 | 6/2003 | Goble et al. |
| 6,602,243 B2 | 8/2003 | Noda |
| 6,602,252 B2 | 8/2003 | Mollenauer |
| 6,611,793 B1 | 8/2003 | Burnside et al. |
| 6,620,157 B1 | 9/2003 | Dabney et al. |
| 6,620,189 B1 | 9/2003 | Machold et al. |
| 6,623,423 B2 | 9/2003 | Sakurai |
| 6,626,901 B1 | 9/2003 | Treat et al. |
| 6,629,973 B1 | 10/2003 | Wardell et al. |
| 6,632,193 B1 | 10/2003 | Davison et al. |
| 6,635,056 B2 | 10/2003 | Kadhiresan et al. |
| 6,635,057 B2 | 10/2003 | Harano |
| 6,645,198 B1 | 11/2003 | Bommannan et al. |
| 6,648,883 B2 | 11/2003 | Francischelli |
| 6,651,669 B1 | 11/2003 | Burnside |
| 6,652,513 B2 | 11/2003 | Panescu et al. |
| 6,652,514 B2 | 11/2003 | Ellman |
| 6,653,569 B1 | 11/2003 | Sung |
| 6,656,177 B2 | 12/2003 | Truckai et al. |
| 6,663,623 B1 | 12/2003 | Oyama et al. |
| 6,663,624 B2 | 12/2003 | Edwards et al. |
| 6,663,627 B2 | 12/2003 | Francischelli et al. |
| 6,666,860 B1 | 12/2003 | Takahashi |
| 6,672,151 B1 | 1/2004 | Schultz et al. |
| 6,679,875 B2 | 1/2004 | Honda |
| 6,682,527 B2 | 1/2004 | Strul |
| 6,685,700 B2 | 2/2004 | Behl |
| 6,685,701 B2 | 2/2004 | Orszulak et al. |
| 6,685,703 B2 | 2/2004 | Pearson et al. |
| 6,689,131 B2 | 2/2004 | McClurken |
| 6,692,489 B1 | 2/2004 | Heim |
| 6,693,782 B1 | 2/2004 | Lash |
| 6,695,837 B2 | 2/2004 | Howell |
| 6,696,844 B2 | 2/2004 | Wong et al. |
| 6,712,813 B2 | 3/2004 | Ellman |
| 6,723,091 B2 | 4/2004 | Goble et al. |
| 6,730,078 B2 | 5/2004 | Simpson et al. |
| 6,730,079 B2 | 5/2004 | Lovewell |
| 6,730,080 B2 | 5/2004 | Harano |
| 6,733,495 B1 | 5/2004 | Bek |
| 6,733,498 B2 | 5/2004 | Paton |
| 6,740,079 B1 | 5/2004 | Eggers |
| 6,740,085 B2 | 5/2004 | Hareyama |
| 6,743,225 B2 | 6/2004 | Sanchez et al. |
| 6,746,284 B1 | 6/2004 | Spink, Jr. |
| 6,749,624 B2 | 6/2004 | Knowlton |
| 6,755,825 B2 | 6/2004 | Shoenman et al. |
| 6,758,846 B2 | 7/2004 | Goble et al. |
| 6,761,716 B2 | 7/2004 | Kadhiresan et al. |
| 6,778,044 B2 | 8/2004 | Fehrenbach et al. |
| 6,783,523 B2 | 8/2004 | Qin |
| 6,784,405 B2 | 8/2004 | Flugstad et al. |
| 6,786,905 B2 | 9/2004 | Swanson et al. |
| 6,790,206 B2 | 9/2004 | Panescu |
| 6,792,390 B1 | 9/2004 | Burnside et al. |
| 6,796,980 B2 | 9/2004 | Hall |
| 6,796,981 B2 | 9/2004 | Wham |
| 6,809,508 B2 | 10/2004 | Donofrio |
| 6,818,000 B2 | 11/2004 | Muller et al. |
| 6,824,539 B2 | 11/2004 | Novak |
| 6,830,569 B2 | 12/2004 | Thompson |
| 6,837,888 B2 | 1/2005 | Ciarrocca et al. |
| 6,843,682 B2 | 1/2005 | Matsuda et al. |
| 6,843,789 B2 | 1/2005 | Goble |
| 6,849,073 B2 | 2/2005 | Hoey |
| 6,855,141 B2 | 2/2005 | Lovewell |
| 6,855,142 B2 | 2/2005 | Harano |
| 6,860,881 B2 | 3/2005 | Sturm |
| 6,864,686 B2 | 3/2005 | Novak |
| 6,875,210 B2 | 4/2005 | Refior |
| 6,890,331 B2 | 5/2005 | Kristensen |
| 6,893,435 B2 | 5/2005 | Goble |
| 6,899,538 B2 | 5/2005 | Matoba |
| 6,923,804 B2 | 8/2005 | Eggers et al. |
| 6,929,641 B2 | 8/2005 | Goble et al. |
| 6,936,047 B2 | 8/2005 | Nasab et al. |
| 6,939,344 B2 | 9/2005 | Kreindel |
| 6,939,346 B2 | 9/2005 | Kannenberg et al. |
| 6,939,347 B2 | 9/2005 | Thompson |
| 6,942,660 B2 | 9/2005 | Pantera et al. |
| 6,948,503 B2 | 9/2005 | Refior et al. |
| 6,953,461 B2 | 10/2005 | McClurken et al. |
| 6,958,064 B2 | 10/2005 | Rioux et al. |
| 6,962,587 B2 | 11/2005 | Johnson et al. |

| | | |
|---|---|---|
| 6,966,907 B2 | 11/2005 | Goble |
| 6,970,752 B1 | 11/2005 | Lim et al. |
| 6,974,453 B2 | 12/2005 | Woloszko et al. |
| 6,974,463 B2 | 12/2005 | Magers et al. |
| 6,977,495 B2 | 12/2005 | Donofrio |
| 6,984,231 B2 | 1/2006 | Goble et al. |
| 6,989,010 B2 | 1/2006 | Francischelli et al. |
| 6,994,704 B2 | 2/2006 | Qin et al. |
| 6,994,707 B2 | 2/2006 | Ellman et al. |
| 7,001,379 B2 | 2/2006 | Behl et al. |
| 7,001,381 B2 | 2/2006 | Harano et al. |
| 7,004,174 B2 | 2/2006 | Eggers et al. |
| 7,008,369 B2 | 3/2006 | Cuppen |
| 7,008,417 B2 | 3/2006 | Eick |
| 7,008,421 B2 | 3/2006 | Daniel et al. |
| 7,025,764 B2 | 4/2006 | Paton et al. |
| 7,033,351 B2 | 4/2006 | Howell |
| 7,041,096 B2 | 5/2006 | Malis et al. |
| 7,044,948 B2 | 5/2006 | Keppel |
| 7,044,949 B2 | 5/2006 | Orszulak et al. |
| 7,048,687 B1 | 5/2006 | Reuss et al. |
| 7,060,063 B2 | 6/2006 | Marion et al. |
| 7,062,331 B2 | 6/2006 | Zarinetchi et al. |
| 7,063,692 B2 | 6/2006 | Sakurai et al. |
| 7,066,933 B2 | 6/2006 | Hagg |
| 7,074,217 B2 | 7/2006 | Strul et al. |
| 7,083,618 B2 | 8/2006 | Couture et al. |
| 7,094,231 B1 | 8/2006 | Ellman et al. |
| 7,104,834 B2 | 9/2006 | Robinson et al. |
| RE39,358 E | 10/2006 | Goble |
| 7,115,121 B2 | 10/2006 | Novak |
| 7,115,124 B1 | 10/2006 | Xiao |
| 7,118,564 B2 | 10/2006 | Ritchie et al. |
| 7,122,031 B2 | 10/2006 | Edwards et al. |
| 7,131,445 B2 | 11/2006 | Amoah |
| 7,131,860 B2 | 11/2006 | Sartor et al. |
| 7,137,980 B2 | 11/2006 | Buysse et al. |
| 7,146,210 B2 | 12/2006 | Palti |
| 7,147,638 B2 | 12/2006 | Chapman et al. |
| 7,151,964 B2 | 12/2006 | Desai et al. |
| 7,153,300 B2 | 12/2006 | Goble |
| 7,156,842 B2 | 1/2007 | Sartor et al. |
| 7,156,844 B2 | 1/2007 | Reschke et al. |
| 7,156,846 B2 | 1/2007 | Dycus et al. |
| 7,160,293 B2 | 1/2007 | Sturm et al. |
| 7,163,536 B2 | 1/2007 | Godara |
| 7,166,986 B2 | 1/2007 | Kendall |
| 7,169,144 B2 | 1/2007 | Hoey et al. |
| 7,172,591 B2 | 2/2007 | Harano et al. |
| 7,175,618 B2 | 2/2007 | Dabney et al. |
| 7,175,621 B2 | 2/2007 | Heim et al. |
| 7,192,427 B2 | 3/2007 | Chapelon et al. |
| 7,195,627 B2 | 3/2007 | Amoah et al. |
| 7,200,010 B2 | 4/2007 | Broman et al. |
| 7,203,556 B2 | 4/2007 | Daners |
| 7,211,081 B2 | 5/2007 | Goble |
| 7,214,224 B2 | 5/2007 | Goble |
| 7,217,269 B2 | 5/2007 | El-Galley et al. |
| 7,220,260 B2 | 5/2007 | Fleming et al. |
| 7,223,264 B2 | 5/2007 | Daniel et al. |
| 7,226,447 B2 | 6/2007 | Uchida et al. |
| 7,229,469 B1 | 6/2007 | Witzel et al. |
| 7,232,437 B2 | 6/2007 | Berman et al. |
| 7,233,278 B2 | 6/2007 | Eriksson |
| 7,238,181 B2 | 7/2007 | Daners et al. |
| 7,238,183 B2 | 7/2007 | Kreindel |
| 7,244,255 B2 | 7/2007 | Daners et al. |
| 7,247,155 B2 | 7/2007 | Hoey et al. |
| 7,250,048 B2 | 7/2007 | Francischelli et al. |
| 7,250,746 B2 | 7/2007 | Oswald et al. |
| 7,255,694 B2 | 8/2007 | Keppel |
| 7,258,688 B1 | 8/2007 | Shah et al. |
| 7,282,048 B2 | 10/2007 | Goble et al. |
| 7,282,049 B2 | 10/2007 | Orszulak et al. |
| 7,285,117 B2 | 10/2007 | Krueger et al. |
| 7,294,127 B2 | 11/2007 | Leung et al. |
| 7,300,435 B2 | 11/2007 | Wham et al. |
| 7,300,437 B2 | 11/2007 | Pozzato |
| 7,303,557 B2 | 12/2007 | Wham et al. |
| 7,305,311 B2 | 12/2007 | Van Zyl |
| 7,311,703 B2 | 12/2007 | Turovskiy et al. |
| 7,317,954 B2 | 1/2008 | McGreevy |
| 7,317,955 B2 | 1/2008 | McGreevy |
| 7,324,357 B2 | 1/2008 | Miura et al. |
| 7,333,859 B2 | 2/2008 | Rinaldi et al. |
| 7,341,586 B2 | 3/2008 | Daniel et al. |
| 7,344,532 B2 | 3/2008 | Goble et al. |
| 7,353,068 B2 | 4/2008 | Tanaka et al. |
| 7,354,436 B2 | 4/2008 | Rioux et al. |
| 7,357,800 B2 | 4/2008 | Swanson |
| 7,364,577 B2 | 4/2008 | Wham et al. |
| 7,364,578 B2 | 4/2008 | Francischelli et al. |
| 7,364,972 B2 | 4/2008 | Ono et al. |
| 7,367,972 B2 | 5/2008 | Francischelli et al. |
| RE40,388 E | 6/2008 | Gines |
| 7,396,336 B2 | 7/2008 | Orszulak et al. |
| 7,402,754 B2 | 7/2008 | Kirwan, Jr. et al. |
| D574,323 S | 8/2008 | Waaler |
| 7,407,502 B2 | 8/2008 | Strul et al. |
| 7,416,437 B2 | 8/2008 | Sartor et al. |
| 7,416,549 B2 | 8/2008 | Young et al. |
| 7,422,582 B2 | 9/2008 | Malackowski et al. |
| 7,422,586 B2 | 9/2008 | Morris et al. |
| 7,425,835 B2 | 9/2008 | Eisele |
| 7,465,302 B2 | 12/2008 | Odell et al. |
| 7,470,272 B2 | 12/2008 | Mulier et al. |
| 7,477,080 B1 | 1/2009 | Fest |
| 7,479,140 B2 | 1/2009 | Ellman et al. |
| 7,491,199 B2 | 2/2009 | Goble |
| 7,491,201 B2 | 2/2009 | Shields et al. |
| 7,503,917 B2 | 3/2009 | Sartor et al. |
| 7,513,896 B2 | 4/2009 | Orszulak |
| 7,517,351 B2 | 4/2009 | Culp et al. |
| 7,525,398 B2 | 4/2009 | Nishimura et al. |
| 7,582,084 B2 | 9/2009 | Swanson et al. |
| 7,628,786 B2 | 12/2009 | Plaven et al. |
| 7,648,499 B2 | 1/2010 | Orszulak et al. |
| 7,651,492 B2 | 1/2010 | Wham |
| 7,651,493 B2 | 1/2010 | Arts et al. |
| 7,655,003 B2 | 2/2010 | Lorang et al. |
| 7,678,105 B2 | 3/2010 | McGreevy et al. |
| 7,722,601 B2 | 5/2010 | Wham et al. |
| 7,731,717 B2 | 6/2010 | Odom et al. |
| 7,736,358 B2 | 6/2010 | Shores et al. |
| 7,749,217 B2 | 7/2010 | Podhajsky |
| 7,766,693 B2 | 8/2010 | Sartor et al. |
| 7,766,905 B2 | 8/2010 | Paterson et al. |
| 2002/0029036 A1 | 3/2002 | Goble et al. |
| 2003/0181898 A1 | 9/2003 | Bowers |
| 2004/0015159 A1 | 1/2004 | Slater et al. |
| 2004/0030330 A1 | 2/2004 | Brassell et al. |
| 2004/0068304 A1 | 4/2004 | Paton |
| 2004/0097912 A1 | 5/2004 | Gonnering |
| 2004/0133189 A1 | 7/2004 | Sakurai |
| 2004/0143263 A1 | 7/2004 | Schechter et al. |
| 2004/0172016 A1 | 9/2004 | Bek et al. |
| 2005/0004564 A1 | 1/2005 | Wham |
| 2005/0004634 A1 | 1/2005 | Ricart et al. |
| 2005/0021020 A1 | 1/2005 | Blaha et al. |
| 2005/0109111 A1 | 5/2005 | Manlove et al. |
| 2005/0197659 A1 | 9/2005 | Bahney |
| 2005/0203504 A1 | 9/2005 | Wham et al. |
| 2005/0245921 A1 | 11/2005 | Strul et al. |
| 2006/0015095 A1 | 1/2006 | Desinger et al. |
| 2006/0079774 A1 | 4/2006 | Anderson |
| 2006/0111711 A1 | 5/2006 | Goble |
| 2006/0161148 A1 | 7/2006 | Behnke |
| 2006/0178664 A1 | 8/2006 | Keppel |
| 2006/0224152 A1 | 10/2006 | Behnke et al. |
| 2006/0291178 A1 | 12/2006 | Shih |
| 2007/0038209 A1 | 2/2007 | Buysse et al. |
| 2007/0088413 A1 | 4/2007 | Weber et al. |
| 2007/0093801 A1 | 4/2007 | Behnke |
| 2007/0135812 A1 | 6/2007 | Sartor |
| 2007/0173802 A1 | 7/2007 | Keppel |
| 2007/0173803 A1 | 7/2007 | Wham et al. |
| 2007/0173804 A1 | 7/2007 | Wham et al. |
| 2007/0173805 A1 | 7/2007 | Weinberg et al. |

| | | | | | |
|---|---|---|---|---|---|
| 2007/0173806 A1 | 7/2007 | Orszulak et al. | DE | 3510586 | 10/1986 |
| 2007/0173813 A1 | 7/2007 | Odom | DE | 3604823 | 8/1987 |
| 2007/0203481 A1 | 8/2007 | Gregg et al. | DE | 390937 | 4/1989 |
| 2007/0265612 A1 | 11/2007 | Behnke et al. | DE | 3904558 | 8/1990 |
| 2007/0282320 A1 | 12/2007 | Buysse et al. | DE | 3942998 | 7/1991 |
| 2007/0293858 A1 | 12/2007 | Fischer | DE | 4206433 | 9/1993 |
| 2008/0015563 A1 | 1/2008 | Hoey et al. | DE | 4339049 | 5/1995 |
| 2008/0015564 A1 | 1/2008 | Wham et al. | DE | 19506363 | 8/1996 |
| 2008/0039831 A1 | 2/2008 | Odom et al. | DE | 19717411 | 11/1998 |
| 2008/0082094 A1 | 4/2008 | McPherson et al. | DE | 19848540 | 5/2000 |
| 2008/0082095 A1 | 4/2008 | Shores et al. | EP | 246350 | 11/1987 |
| 2008/0125767 A1 | 5/2008 | Blaha | EP | 267403 | 5/1988 |
| 2008/0177199 A1 | 7/2008 | Podhajsky | EP | 296777 | 12/1988 |
| 2008/0281315 A1 | 11/2008 | Gines | EP | 310431 | 4/1989 |
| 2008/0281316 A1 | 11/2008 | Carlton et al. | EP | 325456 | 7/1989 |
| 2008/0287791 A1 | 11/2008 | Orszulak et al. | EP | 336742 | 10/1989 |
| 2008/0287838 A1 | 11/2008 | Orszulak et al. | EP | 390937 | 10/1990 |
| 2009/0018536 A1 | 1/2009 | Behnke | EP | 556705 | 8/1993 |
| 2009/0024120 A1 | 1/2009 | Sartor | EP | 569130 | 11/1993 |
| 2009/0036883 A1 | 2/2009 | Behnke | EP | 608609 | 8/1994 |
| 2009/0069801 A1 | 3/2009 | Jensen et al. | EP | 694291 | 1/1996 |
| 2009/0082765 A1 | 3/2009 | Collins et al. | EP | 836868 | 4/1998 |
| 2009/0157071 A1 | 6/2009 | Wham et al. | EP | 878169 | 11/1998 |
| 2009/0157072 A1 | 6/2009 | Wham et al. | EP | 882955 | 12/1998 |
| 2009/0157073 A1 | 6/2009 | Orszulak | EP | 1051948 | 11/2000 |
| 2009/0157075 A1 | 6/2009 | Wham et al. | EP | 1053720 | 11/2000 |
| 2009/0234350 A1 | 9/2009 | Behnke et al. | EP | 1151725 | 11/2001 |
| 2009/0237169 A1 | 9/2009 | Orszulak | EP | 1278007 | 1/2003 |
| 2009/0248003 A1 | 10/2009 | Orszulak | EP | 1293171 | 3/2003 |
| 2009/0248006 A1 | 10/2009 | Paulus et al. | EP | 1472984 | 11/2004 |
| 2009/0254077 A1 | 10/2009 | Craig | EP | 1495712 | 1/2005 |
| 2009/0259224 A1 | 10/2009 | Wham et al. | EP | 1500378 | 1/2005 |
| 2009/0292283 A1 | 11/2009 | Odom | EP | 1535581 | 6/2005 |
| 2009/0306648 A1 | 12/2009 | Podhajsky et al. | EP | 1609430 | 12/2005 |
| 2010/0030210 A1 | 2/2010 | Paulus | EP | 1366724 | 1/2006 |
| 2010/0042093 A9 | 2/2010 | Wham et al. | EP | 1707144 | 3/2006 |
| 2010/0057076 A1 | 3/2010 | Behnke et al. | EP | 1645235 | 4/2006 |
| 2010/0063494 A1 | 3/2010 | Orszulak | EP | 880220 | 6/2006 |
| 2010/0063497 A1 | 3/2010 | Orszulak | EP | 1681026 | 7/2006 |
| 2010/0068949 A1 | 3/2010 | Plaven et al. | EP | 1707143 | 10/2006 |
| 2010/0079215 A1 | 4/2010 | Brannan et al. | EP | 1744354 | 1/2007 |
| 2010/0082022 A1 | 4/2010 | Haley et al. | EP | 1776929 | 4/2007 |
| 2010/0082023 A1 | 4/2010 | Brannan et al. | EP | 1810628 | 7/2007 |
| 2010/0082024 A1 | 4/2010 | Brannan et al. | EP | 1810630 | 7/2007 |
| 2010/0082025 A1 | 4/2010 | Brannan et al. | EP | 1810633 | 7/2007 |
| 2010/0082083 A1 | 4/2010 | Brannan et al. | EP | 1810634 | 7/2007 |
| 2010/0082084 A1 | 4/2010 | Brannan et al. | EP | 1854423 | 11/2007 |
| 2010/0094271 A1 | 4/2010 | Ward et al. | EP | 1862137 | 12/2007 |
| 2010/0094275 A1 | 4/2010 | Wham | FR | 1275415 | 10/1961 |
| 2010/0094285 A1 | 4/2010 | Arts et al. | FR | 1347865 | 11/1963 |
| 2010/0094288 A1 | 4/2010 | Kerr | FR | 2313708 | 12/1976 |
| 2010/0179529 A1 | 7/2010 | Podhajsky et al. | FR | 2364461 | 7/1978 |
| 2010/0179533 A1 | 7/2010 | Podhajsky | FR | 2502935 | 10/1982 |
| 2010/0179534 A1 | 7/2010 | Podhajsky et al. | FR | 2517953 | 6/1983 |
| 2010/0179535 A1 | 7/2010 | Podhajsky et al. | FR | 2573301 | 5/1986 |
| 2010/0179536 A1 | 7/2010 | Podhajsky et al. | GB | 607850 | 9/1948 |
| 2010/0179538 A1 | 7/2010 | Podhajsky | GB | 702510 | 1/1954 |
| 2010/0179541 A1 | 7/2010 | Joseph et al. | GB | 855459 | 11/1960 |
| 2010/0179542 A1 | 7/2010 | Joseph et al. | GB | 902775 | 8/1962 |
| 2010/0191233 A1 | 7/2010 | Wham et al. | GB | 2154881 | 9/1985 |
| | | | GB | 2164473 | 3/1986 |
| FOREIGN PATENT DOCUMENTS | | | GB | 2214430 | 9/1989 |
| DE | 1099658 | 2/1961 | GB | 2331247 | 5/1999 |
| DE | 1139927 | 11/1962 | GB | 2358934 | 8/2001 |
| DE | 1149832 | 6/1963 | GB | 2434872 | 8/2007 |
| DE | 1439302 | 1/1969 | SU | 166452 | 1/1965 |
| DE | 2439587 | 2/1975 | SU | 727201 | 4/1980 |
| DE | 2455174 | 5/1975 | WO | WO92/06642 | 4/1992 |
| DE | 2407559 | 8/1975 | WO | WO92/07622 | 5/1992 |
| DE | 2602517 | 7/1976 | WO | WO93/24066 | 12/1993 |
| DE | 2504280 | 8/1976 | WO | WO94/10922 | 5/1994 |
| DE | 2540968 | 3/1977 | WO | WO94/24949 | 11/1994 |
| DE | 2820908 | 11/1978 | WO | WO94/28809 | 12/1994 |
| DE | 2803275 | 8/1979 | WO | WO95/09577 | 4/1995 |
| DE | 2823291 | 11/1979 | WO | WO95/19148 | 7/1995 |
| DE | 2946728 | 5/1981 | WO | WO95/25471 | 9/1995 |
| DE | 3143421 | 5/1982 | WO | WO95/25472 | 9/1995 |
| DE | 3045996 | 7/1982 | WO | WO96/02180 | 2/1996 |
| DE | 3120102 | 12/1982 | WO | WO96/04860 | 2/1996 |

| | | |
|---|---|---|
| WO | WO96/08794 | 3/1996 |
| WO | WO96/18349 | 6/1996 |
| WO | WO96/29946 | 10/1996 |
| WO | WO96/39085 | 12/1996 |
| WO | WO96/39086 | 12/1996 |
| WO | WO96/39088 | 12/1996 |
| WO | WO96/39914 | 12/1996 |
| WO | WO97/06739 | 2/1997 |
| WO | WO97/06740 | 2/1997 |
| WO | WO97/06855 | 2/1997 |
| WO | WO97/10763 | 3/1997 |
| WO | WO97/11648 | 4/1997 |
| WO | WO97/17029 | 5/1997 |
| WO | WO97/43971 | 11/1997 |
| WO | WO98/07378 | 2/1998 |
| WO | WO98/18395 | 5/1998 |
| WO | WO98/27880 | 7/1998 |
| WO | WO99/12607 | 3/1999 |
| WO | WO99/56647 | 11/1999 |
| WO | WO00/48672 | 8/2000 |
| WO | WO00/54683 | 9/2000 |
| WO | WO01/01847 | 1/2001 |
| WO | WO02/00129 | 1/2002 |
| WO | WO02/11634 | 2/2002 |
| WO | WO02/32333 | 4/2002 |
| WO | WO02/45589 | 6/2002 |
| WO | WO02/47565 | 6/2002 |
| WO | WO02/053048 | 7/2002 |
| WO | WO02/088128 | 7/2002 |
| WO | WO03/047446 | 6/2003 |
| WO | WO03/090630 | 11/2003 |
| WO | WO03/090635 | 11/2003 |
| WO | WO03/092520 | 11/2003 |
| WO | WO2005/060365 | 11/2003 |
| WO | WO2004/028385 | 4/2004 |
| WO | WO2004/098385 | 4/2004 |
| WO | WO2004/043240 | 5/2004 |
| WO | WO2004/047659 | 6/2004 |
| WO | WO2004/052182 | 6/2004 |
| WO | WO2004/103156 | 12/2004 |
| WO | WO2005/046496 | 5/2005 |
| WO | WO2005/048809 | 6/2005 |
| WO | WO2005/050151 | 6/2005 |
| WO | WO2005/060849 | 7/2005 |
| WO | WO2005/115235 | 12/2005 |
| WO | WO2006/050888 | 5/2006 |
| WO | WO2006/105121 | 10/2006 |
| WO | WO2007/055691 | 5/2007 |
| WO | WO 2007/067522 A2 | 6/2007 |
| WO | WO2007/105963 | 9/2007 |
| WO | WO2008/003058 | 1/2008 |
| WO | WO2008/011575 | 1/2008 |
| WO | WO2008/043999 | 4/2008 |
| WO | WO2008/044000 | 4/2008 |
| WO | WO2008/044013 | 4/2008 |
| WO | WO2008/070562 | 6/2008 |
| WO | WO2008/071914 | 6/2008 |
| WO | WO2008/110756 | 9/2008 |

OTHER PUBLICATIONS

U.S. Appl. No. 10/406,690, filed Apr. 3, 2003.
U.S. Appl. No. 10/573,713, filed Mar. 28, 2006.
U.S. Appl. No. 10/761,524, filed Jan. 21, 2004.
U.S. Appl. No. 11/242,458, filed Oct. 3, 2005.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
U.S. Appl. No. 12/619,234, filed Nov. 16, 2009.
U.S. Appl. No. 12/639,210, filed Dec. 16, 2009.
U.S. Appl. No. 12/665,081, filed Dec. 17, 2009.
U.S. Appl. No. 12/712,712, filed Feb. 25, 2010.
U.S. Appl. No. 12/713,956, filed Feb. 26, 2010.
U.S. Appl. No. 12/715,212, filed Mar. 1, 2010.
U.S. Appl. No. 12/754,420, filed Apr. 5, 2010.
U.S. Appl. No. 12/772,345, filed May 3, 2010.
U.S. Appl. No. 12/793,136, filed Jun. 3, 2010.
U.S. Appl. No. 12/823,703, filed Jun. 25, 2010.
U.S. Appl. No. 12/826,879, filed Jun. 30, 2010.
U.S. Appl. No. 12/834,364, filed Jul. 12, 2010.
U.S. Appl. No. 12/845,203, filed Jul. 28, 2010.
Wald et al., "Accidental Burns", JAMA, Aug. 16, 1971, vol. 217, No. 7, pp. 916-921.
Vallfors et al., "Automatically Controlled Bipolar Electrosoagulation-'COA-COMP'" Neurosurgical Review 7:2-3 (1984) pp. 187-190.
Sugita et al., "Bipolar Coagulator with Automatic Thermocontrol" J. Neurosurg., vol. 41, Dec. 1944, pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Burdette et al. "In Vivo Probe Measurement Technique for Determining Dielectric Properties At VHF Through Microwave Frequencies", IEEE Transactions on Microwave Theory and Techniques, vol. MTT-28, No. 4, Apr. 1980 pp. 414-427.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedence" Am. J. MI, Jan. Mar. 1964, pp. 16-27.
Cosman et al., "Methods of Making Nervous System Lesions" in William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences-Yingyong Kexue Xuebao, Shangha CN, vol. 23 No. 2;(Mar. 2005); pp. 160-164.
Chicharo et al. "A Sliding Goertzel Algorith" Aug. 1996, pp. 283-297 Signal Processing, Elsevier Science Publishers B.V. Amsterdam, NL vol. 52 No. 3.
Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.

International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001484.0 dated Jun. 14, 2010.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Feb. 25, 2009.
International Search Report EP08015601.1 dated Dec. 5, 2008.
International Search Report EP08155780 dated Jan. 19, 2009.
International Search Report EP08016540.0 dated Feb. 25, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09009860 dated Dec. 8, 2009.
International Search Report EP09012386 dated Apr. 1, 2010.
International Search Report EP09012388.6 dated Apr. 13, 2010.
International Search Report EP09012389.4 dated Jul. 6, 2010.
International Search Report EP09012391.0 dated Apr. 19, 2010.
International Search Report EP09012392 dated Mar. 30, 2010.
International Search Report EP09012396 dated Apr. 7, 2010.
International Search Report EP09012400 dated Apr. 7, 2010.
International Search Report EP09156861.8 dated Jul. 14, 2009.
International Search Report EP09158915 dated Jul. 14, 2009.
International Search Report EP09164754.5 dated Aug. 21, 2009.
International Search Report EP09169377.0 dated Dec. 15, 2009.
International Search Report EP09169588.2 dated Mar. 2, 2010.
International Search Report EP09169589.0 dated Mar. 2, 2010.
International Search Report EP09172749.5 dated Dec. 4, 2009.
International Search Report EP10001808.4 dated Jun. 21, 2010.
International Search Report EP10150563.4 dated Jun. 10, 2010.
International Search Report EP10150564.2 dated Mar. 29, 2010.
International Search Report EP10150565.9 dated Mar. 12, 2010.
International Search Report EP10150566.7 dated Jun. 10, 2010.
International Search Report EP10150567.5 dated Jun. 10, 2010.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US08/052460 dated Apr. 24, 2008.
International Search Report PCT/US09/46870 dated Jul. 21, 2009.
European Examination Report issued by the European Patent Office in co-pending European Application No. 07 019 174.7 and mailed on Nov. 18, 2010.
Extended European Search Report issued by the European Patent Office in co-pending European Application No. 10 188 190.2 and mailed on Nov. 22, 2010.

TRANSFORMER FOR RF VOLTAGE SENSING

CROSS-REFERENCE TO RELATED APPLICATIONS

This application is a continuation of U.S. patent application Ser. No. 11/529,416, now U.S. Pat. No. 7,794,457 filed on Sep. 28, 2006, the entire disclosure of which is incorporated by reference herein.

BACKGROUND

1. Technical Field

The present disclosure relates to electrosurgical apparatuses, systems and methods. More particularly, the present disclosure is directed to electrosurgical generators including a transformer configured for sensing voltage.

2. Background of Related Art

Energy-based tissue treatment is well known in the art. Various types of energy (e.g., electrical, ultrasonic, microwave, cryo, heat, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A patient return electrode is placed remotely from the active electrode to carry the current back to the generator.

Ablation is most commonly a monopolar procedure that is particularly useful in the field of cancer treatment, where one or more RF ablation needle electrodes (usually of elongated cylindrical geometry) are inserted into a living body. A typical form of such needle electrodes incorporates an insulated sheath from which an exposed (uninsulated) tip extends. When an RF energy is provided between the return electrode and the inserted ablation electrode, RF current flows from the needle electrode through the body. Typically, the current density is very high near the tip of the needle electrode, which tends to heat and destroy surrounding issue.

In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes. When the electrodes are sufficiently separated from one another, the electrical circuit is open and thus inadvertent contact with body tissue with either of the separated electrodes does not cause current to flow.

It is known in the art that electrosurgical generators utilize transformers to sense voltage. However, conventional generators generally include one or more transformers performing redundant functions.

SUMMARY

The present disclosure relates to a multiple-secondary transformer for use in electrosurgical generators. The transformer includes one or more secondary windings allowing the transformer to output a corresponding number of sensed voltage signals to a sensor circuit for subsequent analysis.

According to one aspect of the present disclosure, an electrosurgical system is disclosed. The electrosurgical system includes a multiple-secondary transformer configured for sensing voltage. The multiple-secondary transformer includes a primary winding coupled to an active terminal and a return terminal of the electrosurgical system and a plurality of secondary windings. Each of the secondary windings is configured to transform the radio frequency voltage into a sensed voltage. Each of the secondary windings includes an output coupled to a sensor circuit and configured to transmit the sensed voltage to the sensor circuit.

According to another aspect of the present disclosure an electrosurgical generator is disclosed. The generator includes a radio frequency output stage having an active terminal and a return terminal and configured to generate a radio frequency voltage and a sensor circuit that measures at least one of a tissue property and a radio frequency voltage property. The generator also includes a multiple-secondary transformer having a primary winding coupled to an active terminal and a return terminal of the electrosurgical system and a plurality of secondary windings. Each of the secondary windings is configured to transform the radio frequency voltage into a sensed voltage. Each of the secondary windings includes an output coupled to a sensor circuit and configured to transmit the sensed voltage to the sensor circuit.

A method for is also contemplated by the present disclosure. The method includes the steps of providing a multiple-secondary transformer configured for sensing voltage. The multiple-secondary transformer includes a primary winding coupled to an active terminal and a return terminal of the electrosurgical system and a plurality of secondary windings. Each of the secondary windings includes an output coupled to a sensor circuit. The method also includes the steps of generating a radio frequency voltage at a radio frequency output stage including an active terminal and a return terminal and transforming the radio frequency voltage into a sensed voltage at each of the secondary windings and transmitting the sensed voltage to the sensor circuit via the output.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, foot-switch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
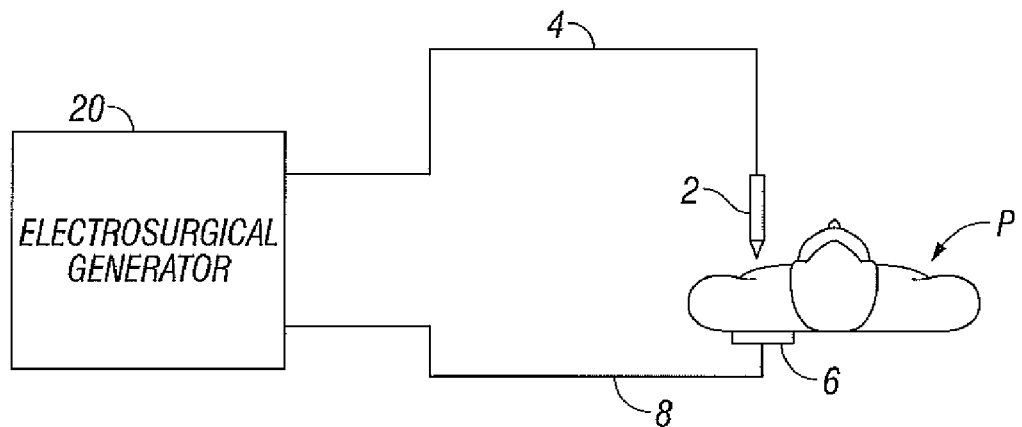
FIGS. 1A-1B are schematic block diagrams of an electrosurgical system according to the present disclosure.

FIG. 1A is a schematic illustration of a monopolar electrosurgical system according to one embodiment of the present disclosure. The system includes an electrosurgical instrument 2 having one or more electrodes for treating tissue of a patient P. The instrument 2 is a monopolar type instrument including one or more active electrodes (e.g., electrosurgical cutting probe, ablation electrode(s), etc.). Electrosurgical RF energy is supplied to the instrument 2 by a generator 20 via an supply line 4, which is connected to an active terminal 30 (FIG. 2) of the generator 20, allowing the instrument 2 to coagulate, seal, ablate and/or otherwise treat tissue. The energy is returned to the generator 20 through a return electrode 6 via a return line 8 at a return terminal 32 (FIG. 2) of the generator 20. The active terminal 30 and the return terminal 32 are connectors configured to interface with plugs (not explicitly shown) of the instrument 2 and the return electrode 6, which are disposed at the ends of the supply line 4 and the return line 8 respectively.

The system may include a plurality of return electrodes 6 that are arranged to minimize the chances of tissue damage by maximizing the overall contact area with the patient P. In addition, the generator 20 and the return electrode 6 may be configured for monitoring so-called "tissue-to-patient" contact to insure that sufficient contact exists therebetween to further minimize chances of tissue damage.

Figure 1B:
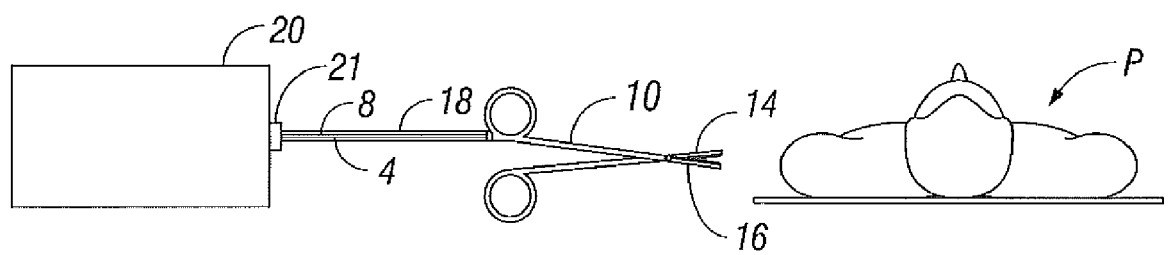
Figure 2:
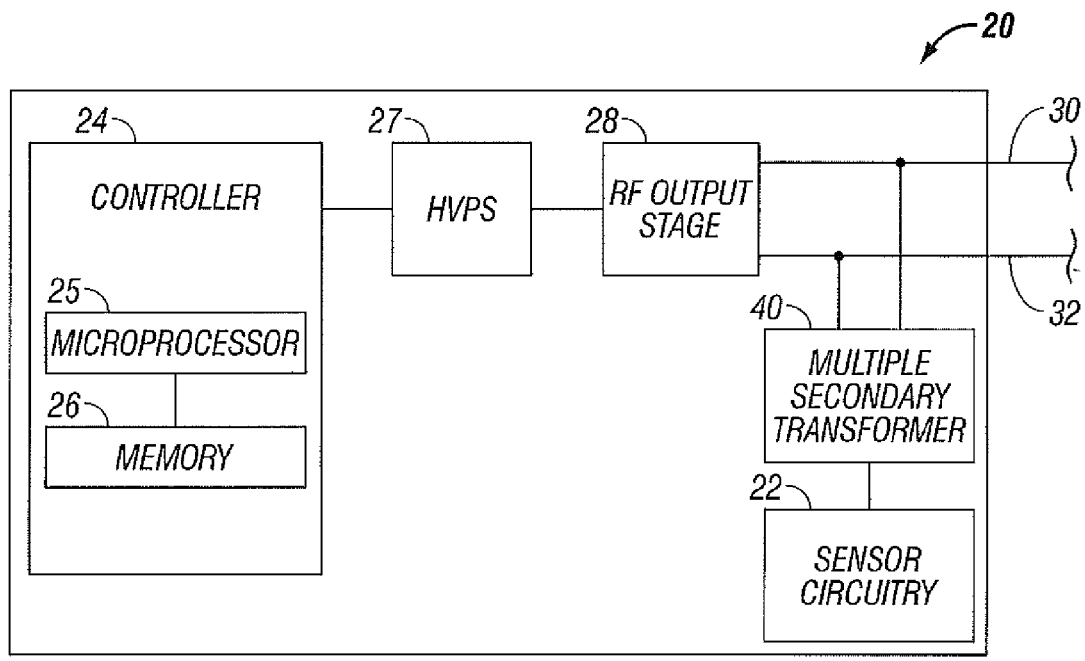
FIG. 2 is a schematic block diagram of a generator according to one embodiment of the present disclosure.

FIG. 1B is a schematic illustration of a bipolar electrosurgical system according to the present disclosure. The system includes a bipolar electrosurgical forceps 10 having one or more electrodes for treating tissue of a patient P. The electrosurgical forceps 10 include opposing jaw members having an active electrode 14 and a return electrode 16 disposed therein. The active electrode 14 and the return electrode 16 are connected to the generator 20 through cable 18, which includes the supply and return lines 4, 8 coupled to the active and return terminals 30, 32, respectively (FIG. 2). The electrosurgical forceps 10 are coupled to the generator 20 at a connector 21 having connections to the active and return terminals 30 and 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform, and other parameters to achieve the desired waveform suitable for a particular task (e.g., coagulating, tissue sealing, intensity setting, etc.). The instrument 2 may also include a plurality of input controls that may be redundant with certain input controls of the generator 20. Placing the input controls at the instrument 2 allows for easier and faster modification of RF energy parameters during the surgical procedure without requiring interaction with the generator 20.

FIG. 2 shows a schematic block diagram of the generator 20 having a controller 24, a high voltage DC power supply 27 ("HVPS") and an RF output stage 28. The HVPS 27 is connected to a conventional AC source (e.g., electrical wall outlet) and provides high voltage DC power to an RF output stage 28, which then converts high voltage DC power into RF energy and delivers the RF energy to the active terminal 30. The energy is returned thereto via the return terminal 32.

In particular, the RF output stage 28 generates sinusoidal waveforms of high RF energy. The RF output stage 28 is configured to generate a plurality of waveforms having various duty cycles, peak voltages, crest factors, and other suitable parameters. Certain types of waveforms are suitable for specific electrosurgical modes. For instance, the RF output stage 28 generates a 100% duty cycle sinusoidal waveform in cut mode, which is best suited for ablating, fusing and dissecting tissue and a 1-25% duty cycle waveform in coagulation mode, which is best used for cauterizing tissue to stop bleeding.

The generator 20 may include a plurality of connectors to accommodate various types of electrosurgical instruments (e.g., instrument 2, electrosurgical forceps 10, etc.). Further, the generator 20 is configured to operate in a variety of modes such as ablation, monopolar and bipolar cutting coagulation, etc. It is envisioned that the generator 20 may include a switching mechanism (e.g., relays) to switch the supply of RF energy between the connectors, such that, for instance, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the HVPS 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A closed loop control scheme is a feedback control loop wherein sensor circuit 22, which may include a plurality of sensors measuring a variety of tissue and energy properties (e.g., tissue impedance, tissue temperature, output current and/or voltage, etc.), provides feedback to the controller 24. Such sensors are within the purview of those skilled in the art. The controller 24 then signals the HVPS 27 and/or RF output stage 28, which then adjust DC and/or RF power supply, respectively. The controller 24 also receives input signals from the input controls of the generator 20 or the instrument 2. The controller 24 utilizes the input signals to adjust power outputted by the generator 20 and/or performs other control functions thereon.

In various types of control loops it may be desirable to measure certain properties of RF energy being delivered by the RF output stage 28. In particular, voltage is continuously measured and delivered to the sensor circuit 22 (e.g., calculating impedance at the surgical site). A multiple-secondary transformer 40 is coupled between the RF output stage 28 and the active and return terminals 30, 32. The transformer 40 provides voltage signals to the sensor circuit 22. In conventional generators, multiple sense transformers are used to serve as voltage sensors for multiple purposes, such as primary voltage sense (e.g., calculating tissue and RF energy properties) and secondary voltage sense (e.g. dosage error calculation, single fault protection). In contrast, the transformer 40, according to the teachings of one embodiment of the present disclosure, is configured to output multiple sense voltages obviating the need for multiple sense transformers.

Figure 3:
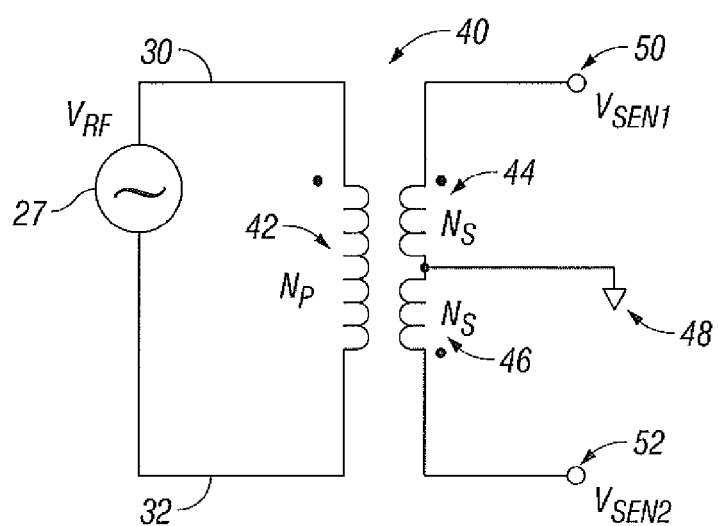
FIG. 3 is an electrical schematic diagram of a multiple-secondary transformer according to the present disclosure.

FIG. 3 shows an electrical schematic diagram of the transformer 40 coupled to the active and return terminals 30 and 32 of the RF output stage 27. The RF output stage 27 generates a radio frequency voltage ($V_{RF}$) suitable for performing electrosurgical procedures (e.g., coagulation, ablation, etc.). The transformer 40 transforms the $V_{RF}$ to desired sensed voltage, in particular, the sensed voltages $V_{SEN1}$ and $V_{SEN2}$. The transformer 40 includes a primary winding 42, which is in circuit with the output of the RF output stage 27, and a plurality of secondary windings 44 and 46 in circuit with sensor circuit outputs 50 and 52 respectively. The transformer 40 is also connected to a sensor circuit return 48, which serves as a ground connection. The transformer 40 may be also configured for differential measurement thereby obviating the need for a ground connection. Having multiple secondary windings allows the transformer 40 to output multiple $V_{SEN}$ voltages to the sensor circuit 22. Thus, $V_{SEN1}$ may be used as primary sensed voltage for determining impedance of the tissue and $V_{SEN2}$ may be used as secondary sensed voltage for monitoring various error conditions.

The primary winding 42 includes a predetermined number of primary turns $N_P$ and the secondary windings 44 and 46 include a number of secondary turns $N_S$. If $N_S$ is the same for each of the secondary windings 44 and 46, the turns ratio ($N_P/N_S$), which determines the step-down ratio of the transformer 40, is also the same. This allows the transformer 40 to output equivalent $V_{SEN1}$ and $V_{SEN2}$ for a uniform $V_{RF}$. $N_s$ may be different for each of the secondary circuits 44 and 46 allowing for different step-down ratios and, hence, different $V_{SEN}$.

The transformer 40 may include multiple secondary windings (e.g., three or four) depending on the number of sensed voltages to be monitored by the sensor circuit 22. The secondary circuits of the transformer 40 may be modular, such that the secondary winding can be switched "in" and "out" to adjust the step down ration. This will accommodate large variation in RF voltages related to different generator modes.

The transformer 40 provides for many improvements over conventional electrosurgical transformers, such as better coupling due to a single transformer core. Single core configuration also improves accuracy related to dosage errors and provide for a more compact. This in turn reduces the foot print of the circuit as well as the overall mass of the generator 20. A more simplified design also provides for cheaper construction of the generator 20 since a single transformer can perform the same function which was previously performed by multiple transformers.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical generator, comprising:
   a radio frequency output stage coupled to an active terminal and a return terminal and configured to generate a radio frequency voltage;
   a sensor circuit that measures at least one of a tissue property and a radio frequency voltage property; and
   a multiple-secondary transformer including (i) a primary winding having a first lead coupled to the active terminal and a second lead coupled to the return terminal, the first and second leads coupled to the radio frequency output stage and (ii) a plurality of secondary windings, each including an output;
   wherein each of the secondary windings are configured to transform the radio frequency voltage into a sensed voltage and each of the outputs of the secondary windings are coupled to the sensor circuit and configured to transmit the sensed voltage to the sensor circuit.

2. The electrosurgical generator according to claim 1, wherein at least one of the plurality of secondary windings is modular and configured to be selectively engageable with the multiple-secondary transformer.

3. The electrosurgical generator according to claim 1, further comprising an electrosurgical instrument configured to deliver the radio frequency voltage to tissue, the electrosurgical instrument being coupled to the active terminal.

4. The electrosurgical generator according to claim 1, wherein the electrosurgical generator includes a plurality of outputs for interfacing with a plurality of monopolar and bipolar surgical instruments.

5. The electrosurgical generator according to claim 1, wherein the electrosurgical generator includes:
   a plurality of return electrodes configured to minimize tissue damage;
   a plurality of input controls for allowing a user to control the generator; and
   one or more displays for displaying output information.

6. The electrosurgical generator according to claim 1, wherein the radio frequency (RF) output stage is configured to generate sinusoidal waveforms of high RF energy.

7. The electrosurgical generator according to claim 1, wherein the radio frequency (RF) output stage is configured to generate a plurality of waveforms having different ranges of at least one of duty cycles, peak voltages, and crest factors.

8. The electrosurgical generator according to claim 1, wherein the radio frequency (RF) output stage is configured to generate:
   a 100% duty cycle sinusoidal waveform in a cut mode for ablating, fusing, and dissecting tissue; and
   a 1-25% duty cycle waveform in a coagulation mode for cauterizing tissue.

9. The electrosurgical generator according to claim 1, further comprising at least one sensing mechanism in operative communication with at least one feedback mechanism.

10. The electrosurgical generator according to claim 1, wherein the multiple-secondary transformer is configured to output multiple sense voltages.

11. A method for performing electrosurgery, the method comprising:
    providing a radio frequency output stage coupled to an active terminal and a return terminal;
    generating a radio frequency voltage via the radio frequency output stage;
    measuring at least one of a tissue property and a radio frequency voltage property via a sensor circuit; and
    providing a multiple-secondary transformer including (i) a primary winding having a first lead coupled to the active terminal and a second lead coupled to the return terminal, the first and second leads coupled to the radio frequency output stage and (ii) a plurality of secondary windings, each including an output;
    wherein each of the secondary windings are configured to transform the radio frequency voltage into a sensed voltage and each of the outputs of the secondary windings are coupled to the sensor circuit and configured to transmit the sensed voltage to the sensor circuit.

12. The method according to claim 11,
    wherein at least one of the plurality of secondary windings steps down the radio frequency voltage; and
    wherein each of the plurality of secondary windings includes a same number of turns.

13. The method according to claim 11, wherein at least one of the plurality of secondary windings is modular and configured to be selectively engageable with the multiple-secondary transformer.

14. The method according to claim 11, further comprising the steps of:
delivering the radio frequency voltage to tissue via an electrosurgical instrument coupled to the active terminal;
allowing a user to control the generator via a plurality of input controls; and
displaying output information via one or more displays.

15. The method according to claim 11, further comprising the steps of:
providing a plurality of connectors to operatively cooperate with a plurality of surgical instruments; and
switching between the plurality of connectors via a switching mechanism.

16. The method according to claim 11, further comprising the step of providing a sensing mechanism to operatively communicate with a feedback mechanism.

17. The method according to claim 11, wherein the multiple-secondary transformer is configured to output multiple sense voltages.

18. A multiple-secondary transformer, comprising:
a primary winding having a first lead coupled to an active terminal and a second lead coupled to a return terminal, the first and second leads coupled to a radio frequency output stage; and
a plurality of secondary windings, each including an output;
wherein each of the secondary windings are configured to transform radio frequency voltage into a sensed voltage and each of the outputs of the secondary windings are coupled to a sensor circuit and configured to transmit the sensed voltage to the sensor circuit.

19. The multiple-secondary transformer according to claim 18, wherein the multiple-secondary transformer operatively cooperates with the radio frequency output stage coupled to the active terminal and the return terminal and configured to generate the radio frequency voltage.

20. The multiple-secondary transformer according to claim 18, wherein the sensor circuit measures at least one of a tissue property and a radio frequency voltage property.

* * * * *